US00PP09772P

United States Patent [19]

Glicenstein

[11] Patent Number: Plant 9,772

[45] Date of Patent: Dec. 31, 1996

[54] CHRYSANTHEMUM PLANT NAMED 'DREAMY TRACY'

[75] Inventor: Leon Glicenstein, Salinas, Calif.

[73] Assignee: Yoder Brothers, Inc., Barberton, Ohio

[21] Appl. No.: 516,564

[22] Filed: Aug. 18, 1995

[51] Int. Cl.[6] ..... A01H 5/00

[52] U.S. Cl. ..... Plt./82.2

[58] Field of Search ..... Plt./82.2

[56] References Cited

U.S. PATENT DOCUMENTS 4,616,099 10/1986 Sparkes ..... 47/58

OTHER PUBLICATIONS

Broetjes, et al., 1980, "A Mutant of a Mutant of a . . . Irradiation of Progressive Radiation–induced Mutants in a Mutation Breeding Programme with *Chrysanthemum morifolium*", Euphytica, 29:525–530.

Gasling, ed., 1979, "The Chrysanthemum Manual—6th Edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced by X–Rays", Am. Soc. Hort. Sci. Proc., pp. 613–620.

Broertjes, 1966, "Mutation Breeding of Chrysanthemums", Euphytica, 15:156–162.

Dowrick, et al., 1966, "The Induction of Mutations in Chrysanthemum Using X– and Gamma Radiation", Euphytica, 15:204–210.

*Primary Examiner*—Howard J. Locker
*Attorney, Agent, or Firm*—Foley & Lardner

[57] ABSTRACT

A Chrysanthemum plant named Dreamy Tracy particularly characterized by its flat capitulum form; daisy capitulum type, with 4 to 6 layers of ray florets; light yellow ray floret color; diameter across face of capitulum of 54 to 70 mm when fully opened; branching pattern is spreading and prolific; natural season flower date of August 27 to 29 when planting rooted cuttings on June 17 to 21 in Salinas, Calif., and of September 23 to 28 when planting rooted cuttings June 15 to 18 in Hightstown, N.J.; plant height of 20 to 33 cm when grown in fall under natural daylength with no growth regulators; and durable, uniform performance.

1 Drawing Sheet

The present invention comprises a new and distinct cultivar of Chrysanthemum, botanically known as *Dendranthema grandiflora*, and referred to by the cultivar name Dreamy Tracy.

Dreamy Tracy, identified as 9631 (85-095B01), is a product of a mutation induction program. The new cultivar was discovered and selected by inventor Leon Glicenstein on Apr. 9, 1992 in a controlled environment in Salinas, Calif. as one flowering plant within a flowering block established as rooted cuttings from stock plants which had been exposed as unrooted cuttings to an X-ray source of 1750 rads in Fort Myers, Fla. on Nov. 7, 1991. The irradiated parent cultivar was the cultivar Tracy, disclosed in U.S. Plant Pat. No. 8,609 and described as a daisy garden mum with white flower color.

The irradiation program resulting in Dreamy Tracy had as its primary objective the expansion of color ranges of the parent cultivar Tracy. The irradiation program comprised irradiation of cuttings of the parent cultivar at irradiation levels of 1500, 1750 and 2000 rads. A total of 1101 cuttings harvested from a total of 225 irradiated plants were planted on Feb. 24, 10 and 3, 1992, respectively. Of these, 9 initial selections were made, which selections were then revegetated and reflowered. Three consecutive flowerings resulted in discarding 7 of the original 9 selections on Dec. 16, 1992. The remaining selections were maintained as PIs (Possible Introductions) and further trialed in Salinas, Calif., Hightstown, N.J. and Leamington, Ontario, Canada, ultimately resulting in the decision to introduce one selection as Dreamy Tracy, and the other selection as Bright Tracy, disclosed in pending application Ser. No. 08/516,920.

The first act of asexual reproduction of Dreamy Tracy was accomplished when vegetative cuttings were taken from the initial selection in June of 1992 in a controlled environment in Salinas, Calif., by technicians working under supervision of Leon Glicenstein.

Horticultural examination of controlled flowerings of successive plantings has shown that the unique combination of characteristics as herein disclosed for Dreamy Tracy are firmly fixed and are retained through successive generations of asexual reproduction.

Dreamy Tracy has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Dreamy Tracy, which, in combination, distinguish this Chrysanthemum as a new and distinct cultivar:

1. Flat capitulum form.
2. Daisy capitulum type, with 4 to 6 layers of ray florets.
3. Light yellow ray floret color.
4. Diameter across face of capitulum of 54 to 70 mm when fully opened.
5. Branching pattern is spreading and prolific.
6. Natural season flower date of August 27 to 29 when planting rooted cuttings on June 17 to 21 in Salinas, Calif., and of September 23 to 28 when planting rooted cuttings June 15 to 18 in Hightstown, N.J.

7. Plant height of 20 to 33 cm when grown in fall under natural daylength with no growth regulators.

8. Durable, uniform performance.

The accompanying photographic drawing is a color photograph of Dreamy Tracy grown as a pinched garden mum under natural season outside conditions in Salinas, Calif., with the colors being as nearly true as possible with illustrations of this type. Plants were grown outside and dug and transplanted into 15 cm pots at flowering time for photography purposes.

Of the commercial cultivars known to the inventor, the most similar in comparison to Dreamy Tracy is the parent cultivar Tracy. Dreamy Tracy differs from Tracy in ray floret color (light yellow compared to the white ray floret color of Tracy), and Dreamy Tracy consistently flowers 3 to 7 days earlier than Tracy, and has a slightly shorter plant height by 2 to 4 cm. These latter differences also distinguish Dreamy Tracy from sibling cultivar Bright Tracy.

In the following description color references are made to The Royal Horticultural Society Colour Chart. The color values were determined on plant material grown as a pinched garden mum grown outdoors in Salinas, Calif. on Aug. 27, 1994.

Classification:

*Botanical.*—*Dendranthema grandiflora* cv Dreamy Tracy.

*Commercial.*—Flat daisy garden mum.

INFLORESCENCE

A. Capitulum:

*Form.*—Flat.

*Type.*—Daisy.

*Diameter across face.*—54 to 70 mm when fully opened.

B. Corolla of ray florets:

*Color (general tonality from a distance of three meters).*—Light yellow.

*Color (upper surface).*—5D.

*Color (under surface).*—5D.

*Shape.*—Cross-section concave, longitudinal section of outer ray florets slightly convex.

C. Corolla of disc florets:

*Color (mature).*—14B.

*Color (immature).*—14B.

D. Reproductive organs:

*Androecium.*—Present on disc florets only; moderate pollen.

*Gynoecium.*—Present on both ray and disc florets.

PLANT

A. General appearance:

*Height.*—20 to 33 cm when grown in fall under natural daylength with no growth regulators.

*Branching pattern.*—Spreading and prolific.

B. Foliage:

*Color (upper surface).*—147A.

*Color (under surface).*—147B.

*Shape.*—Small, lobed, slightly serrated.

What is claimed is:

1. A new and distinct Chrysanthemum plant named Dreamy Tracy, as described and illustrated.

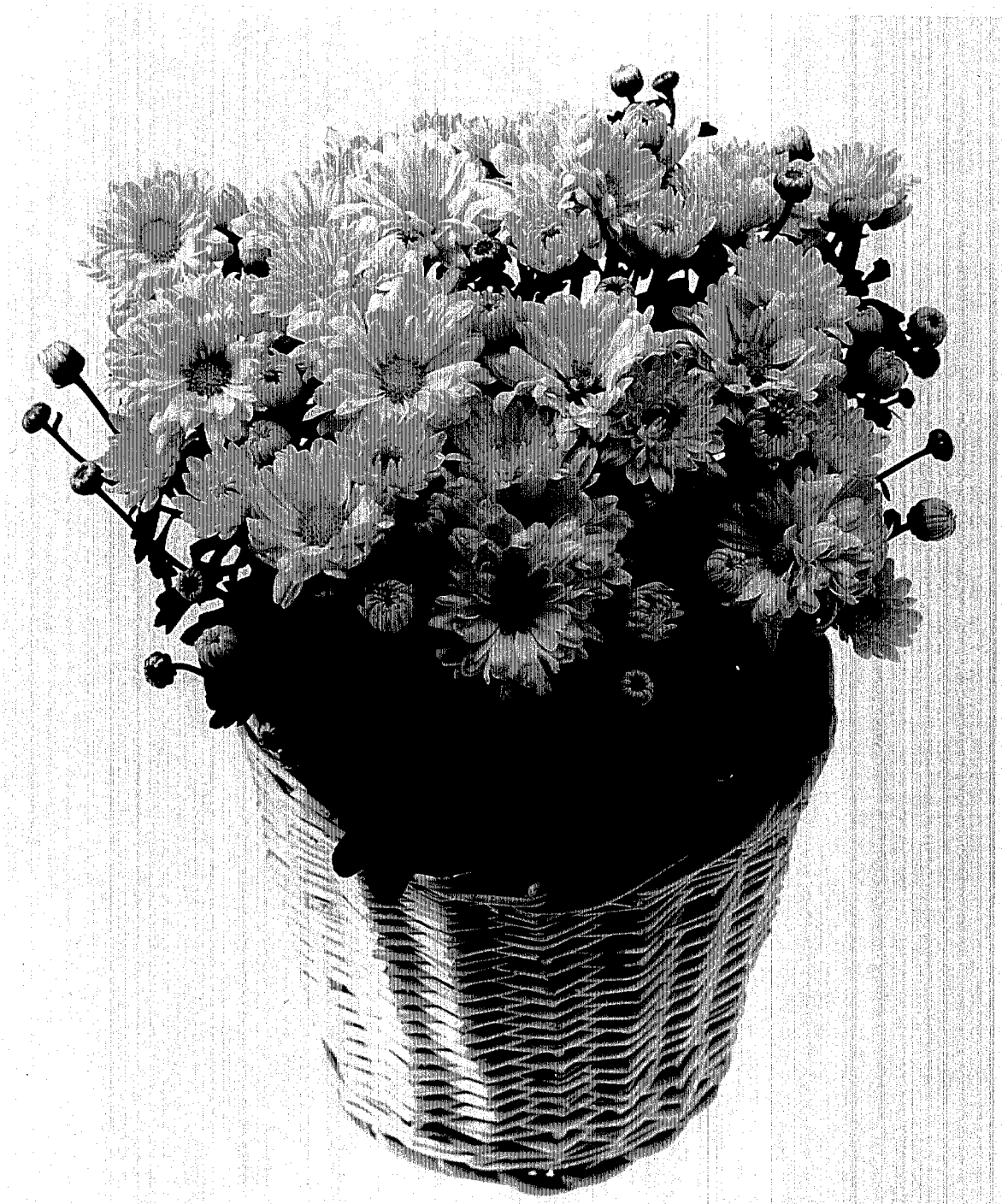

* * * * *